(12) United States Patent
Mori

(10) Patent No.: US 12,076,077 B2
(45) Date of Patent: Sep. 3, 2024

(54) BALLOON-TYPE ELECTRODE CATHETER

(71) Applicant: Japan Lifeline Co., Ltd., Tokyo (JP)

(72) Inventor: Kenji Mori, Tokyo (JP)

(73) Assignee: Japan Lifeline Co., Ltd., Tokyo (JP)

( * ) Notice: Subject to any disclaimer, the term of this patent is extended or adjusted under 35 U.S.C. 154(b) by 829 days.

(21) Appl. No.: 17/120,226

(22) Filed: Dec. 13, 2020

(65) Prior Publication Data

US 2021/0093378 A1 Apr. 1, 2021

Related U.S. Application Data

(63) Continuation of application No. PCT/JP2018/030366, filed on Aug. 15, 2018.

(51) Int. Cl.
*A61B 18/14* (2006.01)
*A61B 18/00* (2006.01)

(52) U.S. Cl.
CPC ...... *A61B 18/1492* (2013.01); *A61B 18/1477* (2013.01); *A61B 2018/00077* (2013.01); *A61B 2018/00083* (2013.01); *A61B 2018/0022* (2013.01); *A61B 2018/00577* (2013.01); *A61B 2018/00744* (2013.01); *A61B 2018/1467* (2013.01); *A61B 2562/0271* (2013.01)

(58) Field of Classification Search
CPC .. A61B 2018/0022; A61B 2018/00744; A61B 2018/00011; A61B 2018/00023; A61B 2018/00166; A61B 2018/00577; A61B 2018/1467; A61B 2018/00214; A61B 2018/00077; A61B 2018/00083; A61B 2018/00005; A61B 2018/00285; A61B 18/1492; A61M 25/1018; A61M 25/0026; A61M 2025/0037; A61M 2025/1056

See application file for complete search history.

(56) References Cited

U.S. PATENT DOCUMENTS 9,402,676 B2 * 8/2016 Babkin ................. A61B 18/02
10,631,930 B1 * 4/2020 Miyagawa ............. A61B 18/24
(Continued)

FOREIGN PATENT DOCUMENTS

CN 107427321 12/2017
JP 2010-268933 12/2010
(Continued)

*Primary Examiner* — Khadijeh A Vahdat
*Assistant Examiner* — Marina Delaney Templeton
(74) *Attorney, Agent, or Firm* — Muramatsu & Associates

(57) ABSTRACT

A balloon-type electrode catheter is capable of performing an ablation treatment with respect to a lesion over a wide area and excellent in an effect of cooling the inner portion of a balloon. The balloon-type electrode catheter includes an outer tube, an energization connector, a balloon having neck portions at both ends of an expansion portion, an inner tube, a distal end tip, strip electrodes formed on the outer surface of the balloon, and a conducting wire that connects each of the strip electrodes and the energization connector to each other. Openings of fluid supply sub lumens of the outer tube are located on the distal end side from an intermediate location in the axial direction in the expansion portion of the balloon. Openings of fluid drainage sub lumens of the outer tube are located at the proximal end of the expansion portion.

10 Claims, 15 Drawing Sheets

(56) References Cited

U.S. PATENT DOCUMENTS

| | | | |
|---|---|---|---|
| 10,905,490 B2* | 2/2021 | Clark | A61B 18/02 |
| 2009/0299355 A1* | 12/2009 | Bencini | A61B 18/02 |
| | | | 606/21 |
| 2010/0241112 A1* | 9/2010 | Watson | A61B 18/02 |
| | | | 606/21 |
| 2012/0289776 A1* | 11/2012 | Keast | A61B 1/2676 |
| | | | 600/114 |
| 2014/0316398 A1* | 10/2014 | Kelly | A61B 18/02 |
| | | | 606/24 |
| 2015/0320472 A1* | 11/2015 | Ghaffari | A61B 18/24 |
| | | | 606/21 |
| 2016/0249969 A1* | 9/2016 | Santoinanni | A61B 18/02 |
| | | | 606/24 |
| 2017/0348049 A1* | 12/2017 | Vrba | A61B 18/1492 |
| 2017/0354463 A1 | 12/2017 | Mori | |
| 2017/0367755 A1 | 12/2017 | Sharma | |
| 2019/0365451 A1* | 12/2019 | Jung, Jr. | A61B 18/02 |

FOREIGN PATENT DOCUMENTS

| | | |
|---|---|---|
| JP | 2013-532564 | 8/2013 |
| JP | 2016-185295 | 10/2016 |
| JP | 2017-113271 | 6/2017 |

\* cited by examiner

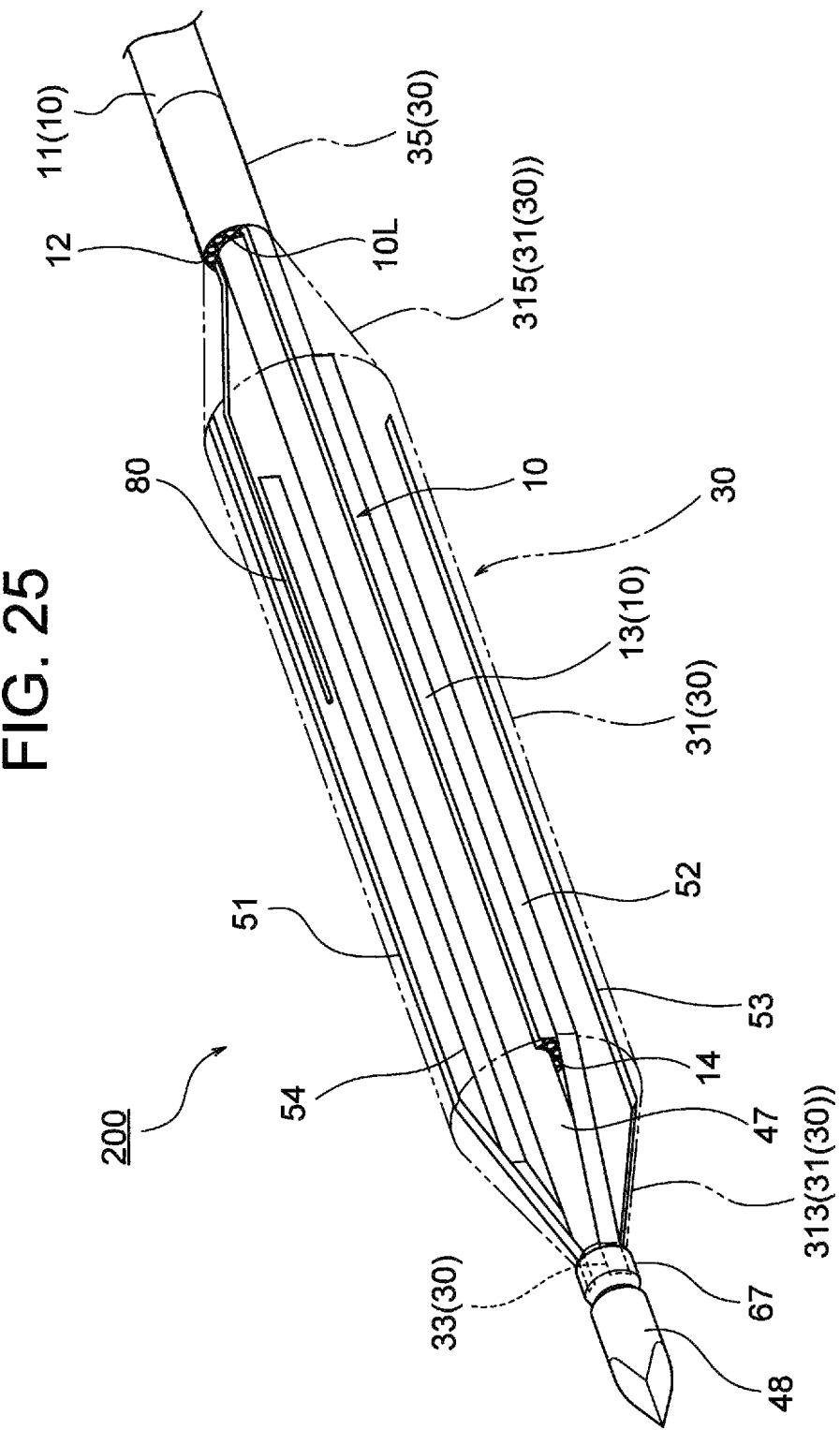

BALLOON-TYPE ELECTRODE CATHETER

This is a continuation of International Application No. PCT/JP2018/030366 filed Aug. 15, 2018, the entire contents of which are incorporated herein by reference.

TECHNICAL FIELD

The present invention relates to a balloon-type electrode catheter for performing a high frequency ablation treatment.

BACKGROUND ART

As a balloon-type electrode catheter (intravascular ablation device) for performing a high frequency ablation treatment of a vessel or tissue around the vessel, hitherto, there has been introduced a balloon-type electrode catheter that is provided with an outer tube (catheter shaft), a balloon connected to the distal end of the outer tube, an inner tube (guide wire lumen) inserted into the lumen of the outer tube and the inner portion of the balloon, a lumen tube (supply lumen) inserted into the lumen of the outer tube to supply a fluid into the inner portion of the balloon, a lumen tube (return lumen) inserted into the lumen of the outer tube to drain the fluid supplied into the inner portion of the balloon, and a surface electrode provided on the outer surface of the balloon (refer to PTL 1 below).

The balloon that constitutes the balloon-type electrode catheter described in PTL 1 has an expansion portion that expands and contracts and a proximal-end-side neck portion and a distal-end-side neck portion that are formed at both ends thereof. The proximal-end-side neck portion is fixed to the outer tube, and the distal-end-side neck portion is fixed to the inner tube (guide wire lumen).

Moreover, in the balloon-type electrode catheter described in PTL 1, the fluid supplied into the inner portion of the balloon by the lumen tube (supply lumen) is circulated in the inner portion of the balloon and drained from the lumen tube (return lumen), thereby cooling the inner portion of the balloon to thereby cool the tissue around the surface electrode.

CITATION LIST

Patent Literature

PTL 1: Japanese Unexamined Patent Application Publication (Translation of PCT Application) No. 2013-532564

SUMMARY OF INVENTION

Technical Problem

However, in the balloon-type electrode catheter described in PTL 1, because both of the lumen tube (supply lumen) and the lumen tube (return lumen) open in the vicinity of the proximal end of the balloon, after the expansion of the balloon, the fluid supplied into the inner portion of the balloon through the opening of the lumen tube (supply lumen) is drained through the opening of the lumen tube (return lumen) immediately without flowing and circulating in the distal end direction. Thus, there is a problem that it is not possible to sufficiently cool the inner portion of the balloon and, consequently, the tissue around the surface electrode.

In particular, to perform an ablation treatment of a tumor and the like by a balloon-type electrode catheter, a high voltage is required to be applied to a surface electrode, and thus, when cooling is insufficient, the tissue around the surface electrode has a high temperature (for example, a temperature over 80° C.) and is easily fiberized. When fiberized tissue is interposed, an ablation treatment after that is substantially impossible.

Further, the balloon-type electrode catheter described in PTL 1 also has a problem that it is difficult to maintain the inner portion of the balloon at a constant pressure (expansion pressure).

The present invention has been made on the basis of the above circumstances.

An object of the present invention is to provide a balloon-type electrode catheter that is capable of performing an ablation treatment over a wide area with respect to a lesion, such as a tumor and the like, and that is excellent in an effect of cooling the inner portion of a balloon and, consequently, an effect of cooling the tissue around a surface electrode.

Another object of the present invention is to provide a balloon-type electrode catheter that is capable of maintaining the inner portion of a balloon at a constant pressure.

Solution to Problem (1) A balloon-type electrode catheter of the present invention is a balloon-type electrode catheter for performing a high frequency ablation treatment, the balloon-type electrode catheter including:

an outer tube that has a center lumen and a plurality of sub lumens that are disposed around the center lumen;

an energization connector that is disposed on a proximal end side of the outer tube;

a balloon that has an expansion portion that expands and contracts and a proximal-end-side neck portion and a distal-end-side neck portion that are continuous with both ends thereof, the balloon being connected to a distal end side of the outer tube as a result of the proximal-end-side neck portion being fixed to a distal end portion of the outer tube and the expansion portion containing the distal end portion of the outer tube;

an inner shaft that is inserted into the center lumen of the outer tube, the inner shaft extending out through an opening of the center lumen into an inner portion of the balloon, being fixed to the distal-end-side neck portion of the balloon, and extending out to an outside of the balloon;

a surface electrode that is formed by a metal thin film that is formed on an outer surface of the balloon at at least the expansion portion of the balloon; and a conducting wire that electrically connects the surface electrode and the energization connector to each other, in which at least one of the sub lumens of the outer tube is a fluid supply sub lumen in which a fluid is caused to flow to supply the fluid into the inner portion of the balloon, in which at least one of the sub lumens of the outer tube is a fluid drainage sub lumen in which the fluid is caused to flow to drain the fluid supplied into the inner portion of the balloon, from the inner portion of the balloon, in which an opening of either one of the fluid supply sub lumen and the fluid drainage sub lumen is located on the distal end side from an intermediate location in an axial direction in the expansion portion, and in which an opening of the other of the fluid supply sub lumen and the fluid drainage sub lumen is located at a proximal end of the expansion portion or in a vicinity thereof.

According to the balloon-type electrode catheter having such a configuration, it is possible to perform an ablation treatment over a wide area with respect to a lesion by the surface electrode formed on the outer surface of the balloon.

In addition, as a result of the opening of either one of the fluid supply sub lumen and the fluid drainage sub lumen being located on the distal end side from the intermediate location in the axial direction in the expansion portion and the opening of the other one of the fluid supply sub lumen and the fluid drainage sub lumen being located at the proximal end or in the vicinity of the proximal end of the expansion portion, that is, as a result of a fluid supply port and a fluid drainage port being displaced from each other in the axial direction, the flow of the fluid in the axial direction is formed, even after the expansion of the balloon (after the inner portion is filled with the fluid), and it is possible to cause the fluid to flow in the inner portion of the balloon. It is thus possible to sufficiently cool the inner portion of the balloon and, consequently, the tissue around the surface electrode.

(2) In the balloon-type electrode catheter of the present invention, preferably, the opening of the fluid supply sub lumen is located on the distal end side from the intermediate location in the axial direction in the expansion portion, and the opening of the fluid drainage sub lumen is located at the proximal end of the expansion portion or in a vicinity thereof.

According to the balloon-type electrode catheter having such a configuration, the flow of the fluid from the distal end side toward the proximal end side in the inner portion of the balloon is formed, even after the expansion of the balloon, and it is possible to cause the fluid to flow in the inner portion of the balloon. It is thus possible to sufficiently cool the inner portion of the balloon and, consequently, the tissue around the surface electrode.

(3) In the aforementioned balloon-type electrode catheter in (2), preferably, the outer tube is formed by a circular tubular part that extends in a proximal end direction from the proximal end of the expansion portion or a location in a vicinity thereof, and a semicircular tubular part that extends in a distal end direction from the proximal end of the expansion portion or a location in the vicinity thereof in an inner portion of the expansion portion beyond the intermediate location in the axial direction in the expansion portion, in which the fluid supply sub lumen is disposed in inner portions of the circular tubular part and the semicircular tubular part and opens in a distal end surface of the semicircular tubular part, and in which the fluid drainage sub lumen is disposed in the inner portion of the circular tubular part and opens in a distal end surface of the circular tubular part.

According to the balloon-type electrode catheter having such a configuration, as a result of the fluid being discharged (supplied) through the opening of the fluid supply sub lumen formed in the distal end surface of the semicircular tubular part, which is the distal end surface of the outer tube, and the fluid being drained through the opening of the fluid drainage sub lumen formed in the distal end surface of the circular tubular part located at the proximal end or in the vicinity of the proximal end of the expansion portion, it is possible to form the flow of the fluid from the distal end side toward the proximal end side in the inner portion of the balloon.

In particular, as a result of the fluid being discharged in the distal end direction through the opening of the fluid supply sub lumen, the fluid comes into contact with the inner wall surface of the distal end part of the expansion portion, which is normally formed to have a cone shape, and then flows in the proximal end direction along the inner wall surface of the expansion portion. It is thereby possible to circulate the fluid in the inner portion of the balloon, and as a result, it is possible to efficiently cool the whole region of the expansion portion.

(4) In the balloon-type electrode catheter of the present invention, preferably, the opening area (when a plurality of the fluid supply sub lumens are present, the total of the areas thereof) of the fluid supply sub lumen is larger than the opening area (when a plurality of the fluid drainage sub lumens are present, the total of the areas thereof) of the fluid drainage sub lumen.

(5) In the balloon-type electrode catheter of the present invention, preferably, the number of the fluid supply sub lumen is greater than the number of the fluid drainage sub lumen.

According to the balloon-type electrode catheter having configurations such as the aforementioned configurations, it is possible to maintain the inner portion of the balloon at a constant pressure (expansion pressure).

(6) Preferably, the inner shaft that constitutes the balloon-type electrode catheter of the present invention is formed by an inner tube that has a lumen into which a guide wire is insertable and that is inserted into the center lumen of the outer tube and extends out through the opening of the center lumen into the inner portion of the balloon, and a distal end tip that has a lumen in communication with the lumen of the inner tube and that is, while being connected to a distal end of the inner tube in the inner portion of the balloon, fixed to the distal-end-side neck portion and extends out to the outside of the balloon.

According to the balloon-type electrode catheter having such a configuration, it is possible to insert and intravascularly introduce the guide wire into the guide wire lumen formed by the inner shaft (the inner tube and the distal end tip) and perform an ablation treatment over a wide area with respect to a vessel or the tissue around the vessel.

(7) In the aforementioned balloon-type electrode catheter in (6), preferably, a distal end portion of the surface electrode extends on an outer surface of the distal-end-side neck portion, the balloon-type electrode catheter is provided with a metal ring electrically connected to the surface electrode by being mounted on the distal-end-side neck portion of the balloon such that an inner circumferential surface of the metal ring is in contact with the distal end portion of the surface electrode, and a distal end of the conducting wire is connected to the inner circumferential surface of the metal ring, the conducting wire extends in the inner portion of the balloon and in the sub lumens of the outer tube, the sub lumens being different from either of the fluid supply sub lumen and the fluid drainage sub lumen, and a proximal end of the conducting wire is connected to the energization connector.

According to the balloon-type electrode catheter having such a configuration, it is possible to electrically connect the surface electrode formed on the outer surface of the balloon to the energization connector via the metal ring and the conducting wire, and it is thus possible to reliably energize the surface electrode with high-frequency current.

In addition, the distal-end-side neck portion of the balloon where the metal ring is mounted is a neck portion fixed to the distal end tip and has an outer diameter that is remarkably small compared with the proximal-end-side neck portion fixed to the outer tube, and thus, the outer diameter of the metal ring mounted on the distal-end-side neck portion is enabled to be smaller than the outer diameter of the outer tube and the outer diameter of the proximal-end-side neck portion.

Consequently, during introduction of the balloon-type electrode catheter, the metal ring is not caught by the openings of a sheath and an endoscope that are used, and insertion properties of the balloon-type electrode catheter with respect to the lumens of the sheath and the endoscope are not impaired.

(8) In the aforementioned balloon-type electrode catheter in (7), preferably, the surface electrode is a plurality of strip electrodes that are formed so as to extend in an axial direction of the balloon and that are disposed in a circumferential direction of the balloon at equal angular intervals, and the inner circumferential surface of the metal ring is in contact with the distal end portion of each of the strip electrodes.

According to the balloon-type electrode catheter having such a configuration, it is possible to electrically connect each of the plurality of strip electrodes formed in the circumferential direction of the balloon at the equal angular intervals to the energization connector via the metal ring and the conducting wire, and it is thus possible to energize each of the plurality of strip electrodes equally with high-frequency current. Consequently, it is possible to perform an ablation treatment of a vessel or the tissue around the vessel homogeneously in the circumferential direction of the vessel.

(9) In the aforementioned balloon-type electrode catheter in (7) or (8), preferably, the metal ring is insulation coated.

According to the balloon-type electrode catheter having such a configuration, it is possible to prevent the metal ring during energization from having a high temperature, and it is possible to avoid the normal tissue around the metal ring from being ablated.

(10) The inner shaft that constitutes the balloon-type electrode catheter of the present invention may be formed by a hollow or solid needle.

According to the balloon-type electrode catheter having such a configuration, it is possible to percutaneously introduce the balloon-type electrode catheter by utilizing the inner shaft (needle), and it is possible to perform an ablation treatment over a wide area by the surface electrode with respect to a lesion, such as a tumor and the like, into which the balloon-type electrode catheter is introduced.

(11) In the balloon-type electrode catheter of the present invention, preferably, the outer diameter of the distal end portion of the outer tube to which the proximal-end-side neck portion of the balloon is fixed is formed to be smaller than the outer diameter of a proximal end portion of the outer tube, and the outer diameter of the proximal-end-side neck portion of the balloon and the outer diameter of the proximal end portion of the outer tube are substantially equal to each other.

According to the balloon-type electrode catheter having such a configuration, the outer diameter of the proximal-end-side neck portion at which the outer diameter is maximum is substantially equal to the outer diameter of the proximal end portion of the outer tube. Thus, insertion properties with respect to the lumens of a sheath and an endoscope are not hindered by this proximal-end-side neck portion.

In addition, the outer diameter of the outer tube can be a maximum diameter restricted by the sheath and the endoscope. It is thus possible to sufficiently ensure the diameters of the fluid supply sub lumen and the fluid drainage sub lumen of the outer tube, and it is possible to further improve the effect of cooling the inner portion of the balloon.

(12) In the balloon-type electrode catheter of the present invention, preferably, a temperature sensor is disposed at a tube wall of the balloon.

Advantageous Effects of Invention

The balloon-type electrode catheter of the present invention is capable of performing a high frequency ablation treatment over a wide area with respect to a lesion, such as a tumor and the like, and excellent in an effect of cooling the inner portion of a balloon and, consequently, an effect of cooling the tissue around the surface electrode, compared with existing balloon-type electrode catheters.

In addition, as a result of the opening area of the fluid supply sub lumen being larger (the number of the sub lumens being increased) than the opening area of the fluid drainage sub lumen, it is possible to stably maintain the pressure (expansion pressure) in the inner portion of the balloon.

BRIEF DESCRIPTION OF DRAWINGS

FIG. 25 is a perspective view illustrating the distal end part of a balloon-type electrode catheter according to another embodiment of the present invention.

DESCRIPTION OF EMBODIMENTS

First Embodiment

Figure 1:
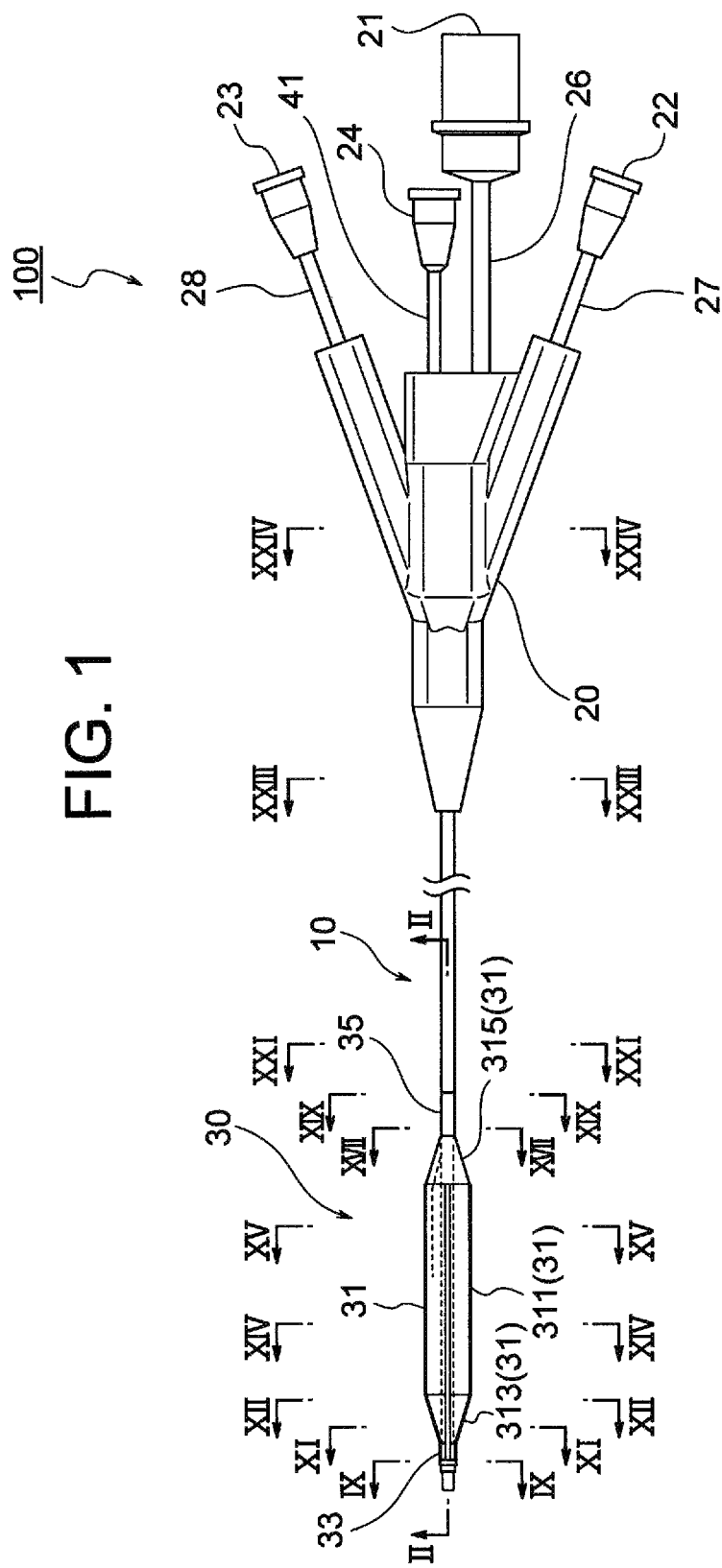
FIG. 1 is a plan view of a balloon-type electrode catheter according to one embodiment of the present invention.

A balloon-type electrode catheter 100 of this embodiment is a balloon-type electrode catheter that is to be intravascularly introduced to treat a lesional tissue, such as a tumor and the like, in a vessel or around the vessel by high frequency ablation.

The balloon-type electrode catheter 100 illustrated in FIG. 1 to FIG. 24 is provided with an outer tube 10 that is formed by a circular tubular part 11 and a semicircular tubular part 13 and that has a center lumen 10L and sub lumens 101L to 112L disposed around the center lumen 10L; an electrical connector 21 disposed on the proximal end side of the outer tube 10; a balloon 30 that has an expansion portion 31 that expands and contracts and neck portions (a distal-end-side neck portion 33 and a proximal-end-side neck portion 35) continuous with both ends thereof, the balloon 30 being connected to the distal end side of the outer tube 10 as a result of the proximal-end-side neck portion 35 being fixed to the circular tubular part 11 that constitutes the distal end portion of the outer tube 10 and the expansion portion 31 containing the semicircular tubular part 13 that constitutes the distal end portion of the outer tube 10; an inner tube 41 that has a guide wire lumen and that is inserted into the center lumen 10L of the outer tube 10 and extends out through the opening of the center lumen 10L into the inner portion of the balloon 30; a distal end tip 46 that has a lumen (guide wire lumen) in communication with the guide wire lumen of the inner tube 41 and that is, while being connected in the inner portion of the balloon 30 to the distal end of the inner tube 41, fixed to the distal-end-side neck portion 33 and extends out to the outside of the balloon 30; strip electrodes 51 to 54 (surface electrodes) formed by a metal thin film formed on the outer surfaces of the expansion portion 31 and the distal-end-side neck portion 33 of the balloon 30; a metal ring 60 that is electrically connected to each of the strip electrodes 51 to 54 by being mounted on the distal-end-side neck portion 33 of the balloon 30 such that the inner circumferential surface thereof is in contact with the distal end portion of each of the strip electrodes 51 to 54; a conducting wire 70 the distal end of which is connected to the inner circumferential surface of the metal ring 60 and extends in the inner portion of the balloon 30 and in the sub lumen 112L of the outer tube 10, and the proximal end of which is connected to the electrical connector 21; and a temperature sensor (thermocouple) 80 the distal end (temperature measuring portion 81) of which is embedded in the tube wall of the expansion portion 31 of the balloon 30 and extends in the tube walls of the expansion portion 31 and the proximal-end-side neck portion 35 and in the lumen 106L of the outer tube 10 (circular tubular part 11), and the proximal end of which is connected to the electrical connector 21.

Figure 2:
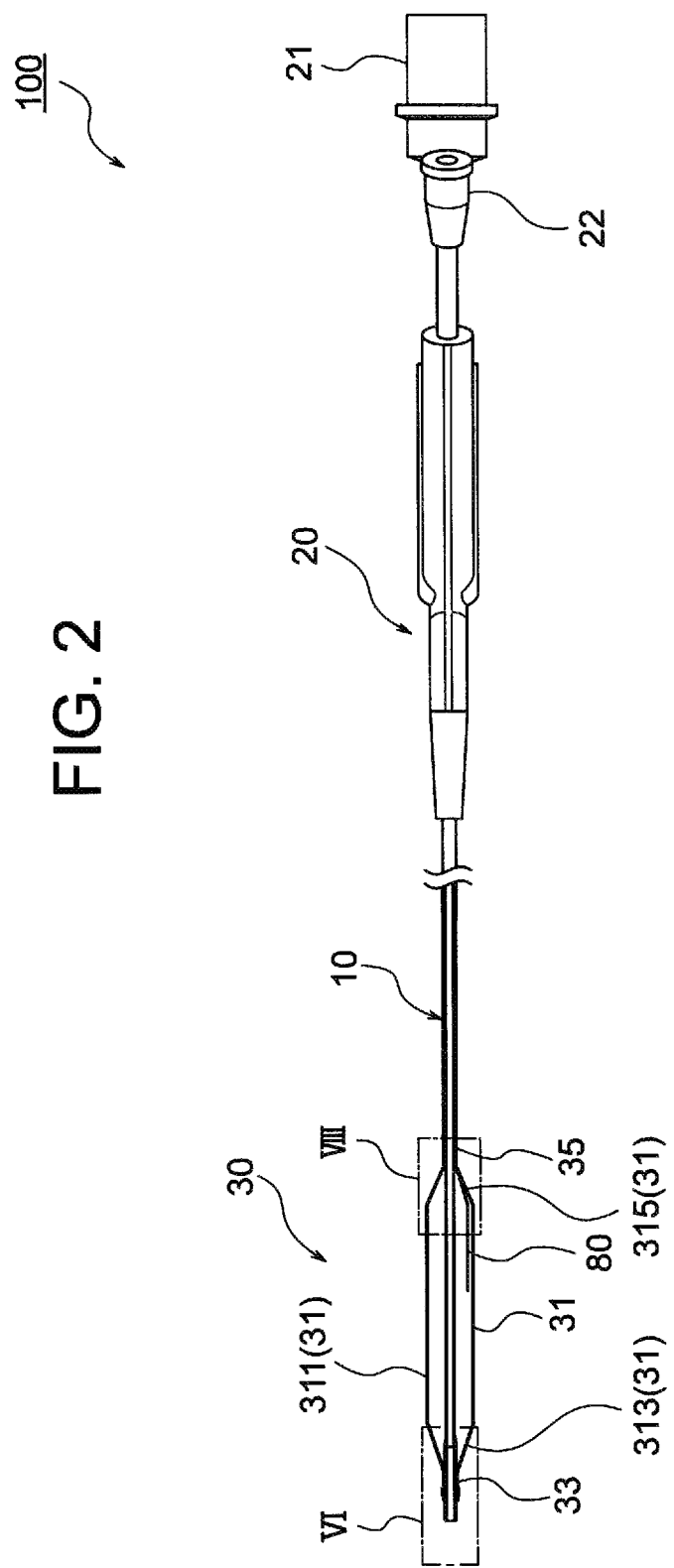
FIG. 2 is a partial cutaway front view (front view including II-II section in FIG. 1) of the balloon-type electrode catheter illustrated in FIG. 1.
Figure 20:
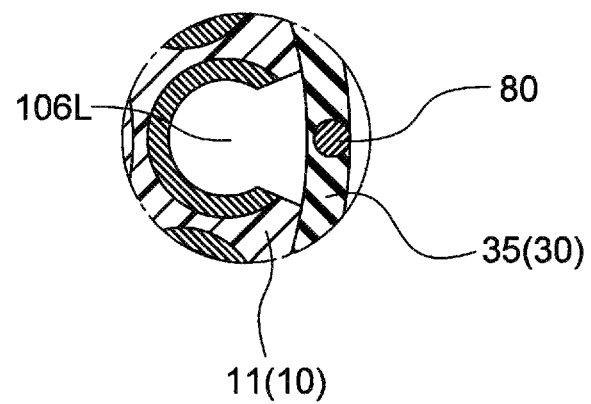
FIG. 20 is a partially enlarged view (XX portion detail illustration) of FIG. 19.

In FIG. 1 and FIG. 2, 20 denotes a Y-connector connected to the proximal end side of the outer tube 10, 22 denotes a fluid supply connector, 23 denotes a fluid drainage connector, 24 denotes a guide wire connector, 26 denotes a conducting-wire protection tube, 27 denotes a fluid supply tube, and 28 denotes a fluid drainage tube.

As illustrated in FIG. 3 to FIG. 5, FIG. 14, FIG. 15, and FIG. 17 to FIG. 22, the outer tube 10 that constitutes the balloon-type electrode catheter 100 is formed by the circular tubular part 11 and the semicircular tubular part 13.

The proximal end portion and one portion of the distal end portion of the outer tube 10 are constituted by the circular tubular part 11, and the distal end portion (excluding the aforementioned one portion) of the outer tube 10 is constituted by the semicircular tubular part 13.

Figure 17:
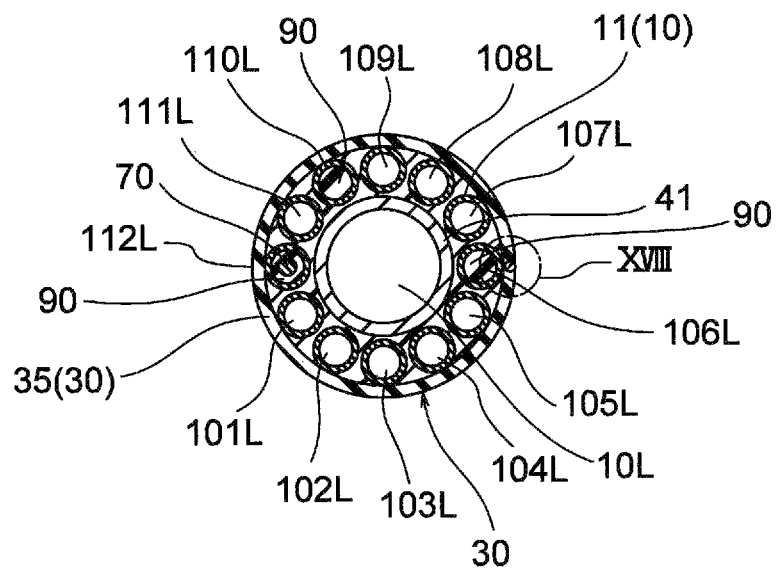
FIG. 17 is a XVII-XVII sectional view of FIG. 1.
Figure 18:
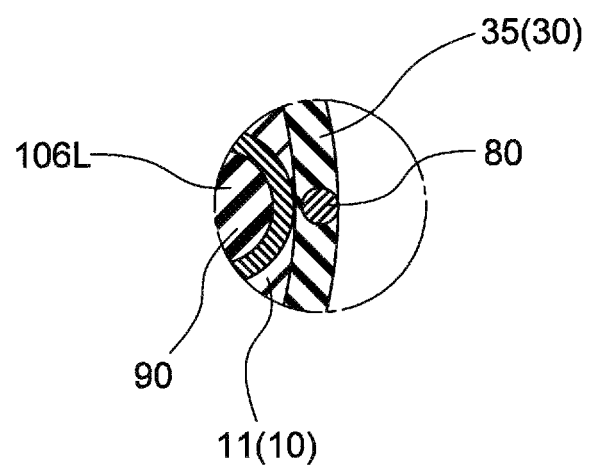
FIG. 18 is a partially enlarged view (XVIII portion detail illustration) of FIG. 17.
Figure 19:
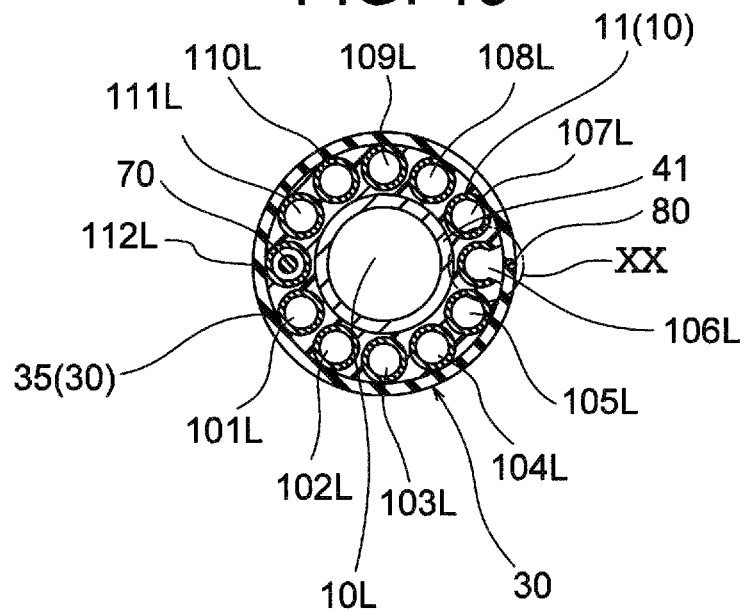
FIG. 19 is a XIX-XIX sectional view of FIG. 1.
Figure 21:
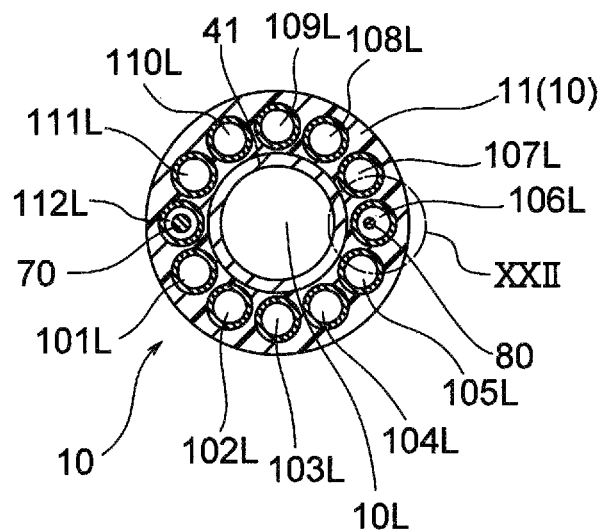
FIG. 21 is a XXI-XXI sectional view of FIG. 1.
Figure 22:
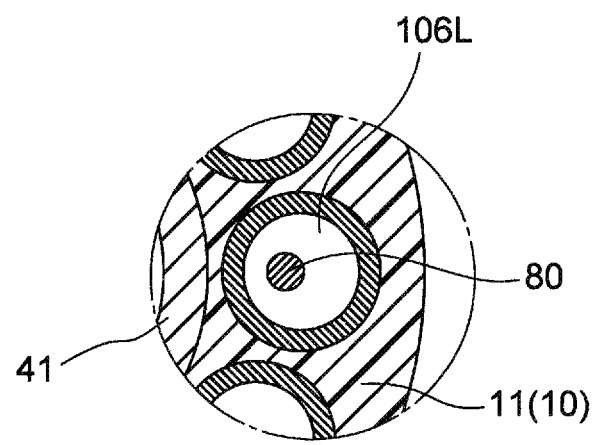
FIG. 22 is a partially enlarged view (XXII portion detail illustration) of FIG. 21.

As illustrated in FIG. 17, FIG. 19, and FIG. 21, in the inner portion of the circular tubular part 11 of the outer tube 10, there are formed the center lumen 10L and the twelve sub lumens 101L to 112L disposed around the center lumen 10L at equal angular (30°) intervals.

In the circular tubular part 11, each of the sub lumens 101L to 112L is formed by a lumen tube that surrounds the sub lumen, and these lumen tubes are fixed by a binder resin that forms the circular tubular part 11.

Figure 14:
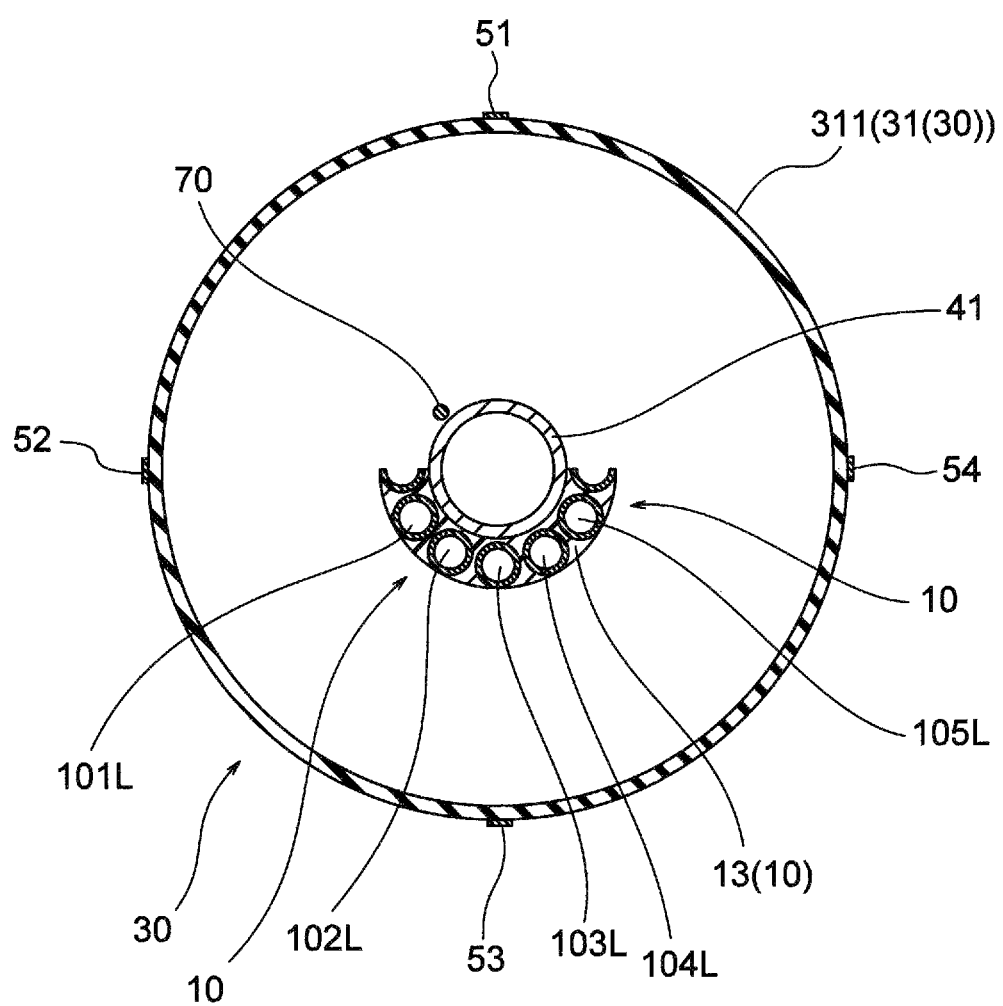
FIG. 14 is a XIV-XIV sectional view of FIG. 1.
Figure 15:
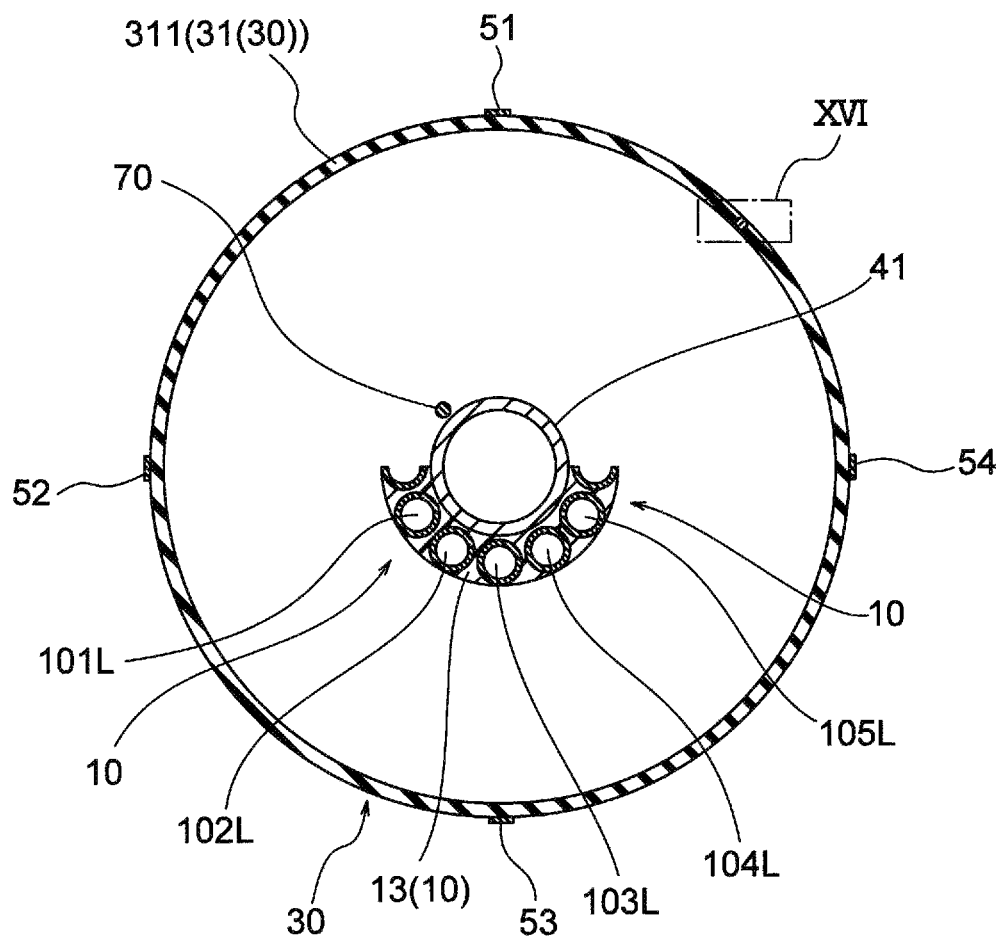
FIG. 15 is a XV-XV sectional view of FIG. 1.
Figure 16:
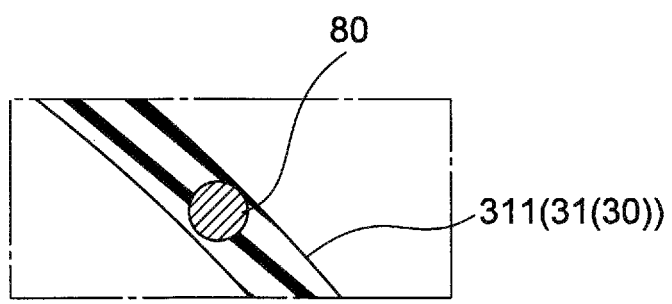
FIG. 16 is a partially enlarged view (XVI portion detail illustration) of FIG. 15.

As illustrated in FIG. 14 and FIG. 15, in the inner portion of the semicircular tubular part 13 of the outer tube 10, the sub lumens 101L to 105L are formed continuously from the inner portion of the circular tubular part 11.

The lumen tubes that surround each of the sub lumens 101L to 105L in the semicircular tubular part 13 are fixed by a binder resin that forms the semicircular tubular part 13.

Figure 3:
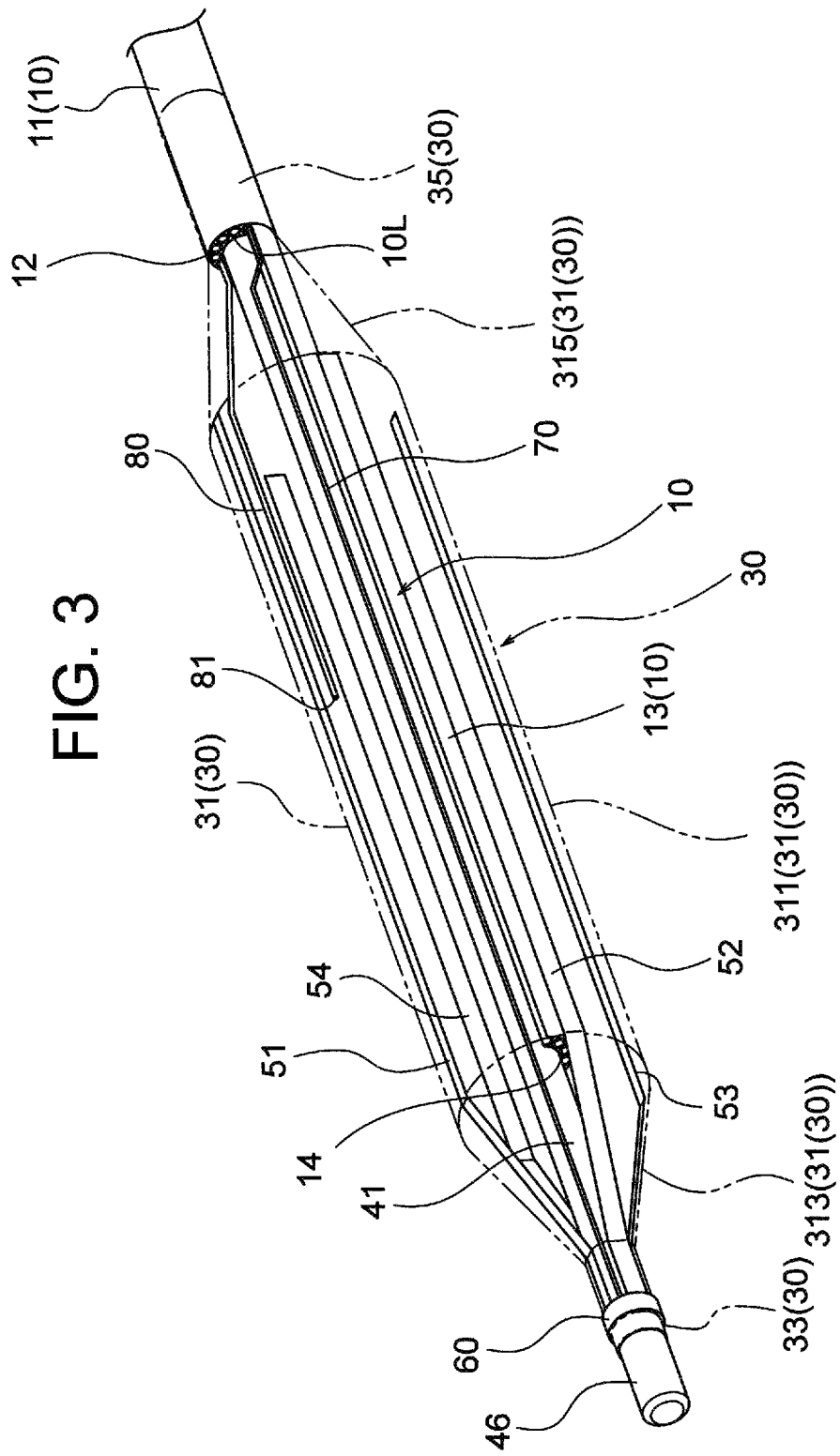
FIG. 3 is a perspective view illustrating the distal end part of the balloon-type electrode catheter illustrated in FIG. 1.
Figure 4:
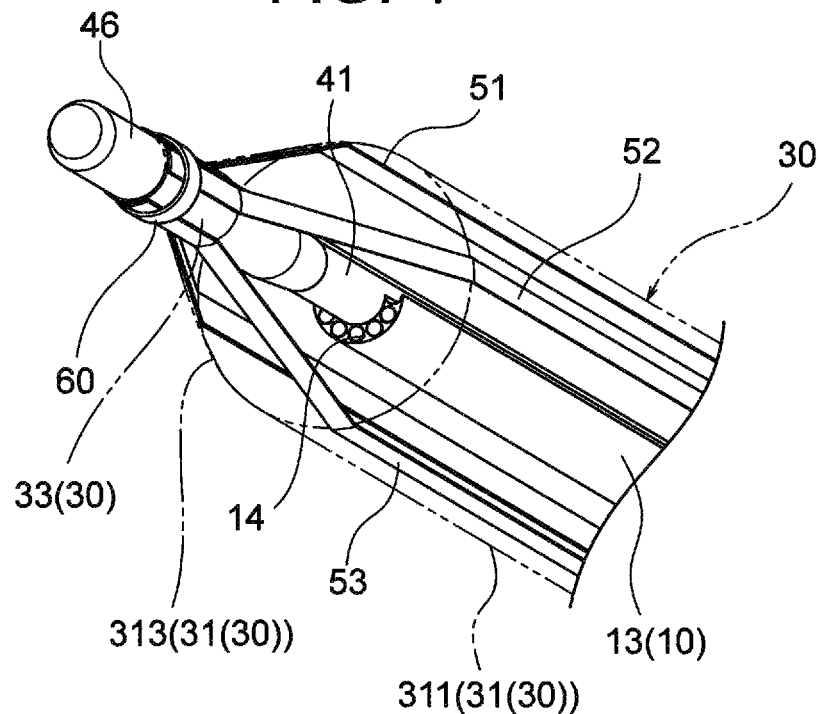
FIG. 4 is a perspective view illustrating the distal end part (the distal end side of the balloon) of the balloon-type electrode catheter illustrated in FIG. 1.

As illustrated in FIG. 3 and FIG. 4, the sub lumens 101L to 105L disposed in the inner portion of the circular tubular part 11 and the inner portion of the semicircular tubular part 13 each open in a distal end surface 14 of the semicircular tubular part 13, the distal end surface 14 being the distal end surface of the outer tube 10.

Each of the sub lumens 101L to 105L is in communication with the fluid supply connector 22 illustrated in FIG. 1 and FIG. 2.

Consequently, the sub lumens 101L to 105L (five sub lumens of the twelve sub lumens formed in the outer tube 10) serve as "fluid supply sub lumens" for supplying a fluid into the inner portion of the balloon 30 (expansion portion 31).

Here, as a fluid to be supplied into the inner portion of the balloon 30, a physiological saline solution can be presented as an example.

The center lumen 10L and the sub lumens 106L to 112L formed in the inner portion of the circular tubular part 11 each open in a distal end surface 12 of the circular tubular part 11.

Note that the openings of the sub lumens 106L, 110L, and 112L are sealed by a seal material 90 illustrated in FIG. 17.

Each of the sub lumens 107L to 111L is in communication with the fluid drainage connector 23 illustrated in FIG. 1.

Consequently, the sub lumens 107L to 109L and 111L (four sub lumens of the twelve sub lumens formed in the outer tube 10) serve as "fluid drainage sub lumens" for draining the fluid supplied into the inner portion of the balloon 30 (expansion portion 31), from the inner portion of the balloon 30.

The constituent material of the outer tube 10 is not particularly limited, and as such a constituent material, for example, polyamide resins, such as polyamide, polyether polyamide, polyether block amide (PEBAX (registered trademark)), nylon, and the like, can be presented. Among these, the PEBAX is preferable.

The outer diameter (the later-described outer diameter at the proximal end portion) of the outer tube 10 is normally 1.0 to 3.3 mm and, when one suitable example is presented, 1.45 mm.

The diameter of the center lumen 10L of the outer tube 10 is normally 0.35 to 0.95 mm and, when one suitable example is presented, 0.85 mm.

The diameters of the sub lumens 101L to 112L of the outer tube 10 are normally 0.10 to 0.75 mm and, when one suitable example is presented, 0.25 mm.

The length of the outer tube 10 is normally 100 to 2200 mm and, when one suitable example is presented, 1800 mm.

As illustrated in FIG. 1 and FIG. 2, the Y-connector 20 is connected to the proximal end side of the outer tube 10.

Figure 23:
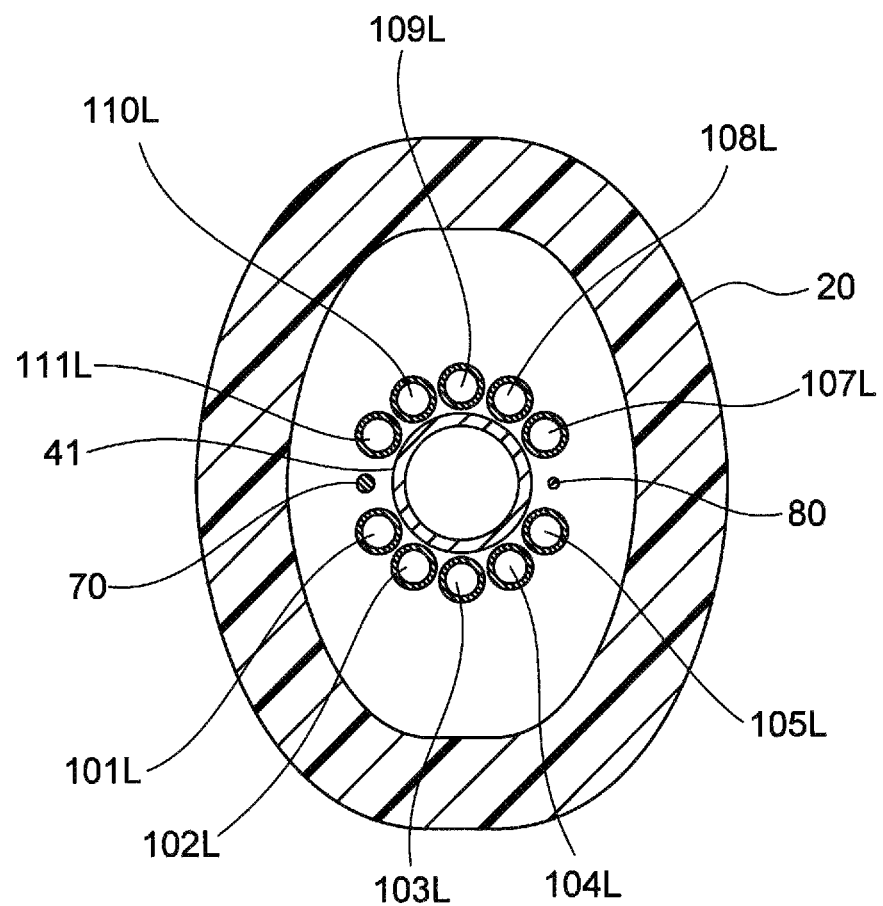
FIG. 23 is a XXIII-XXIII sectional view of FIG. 1.

As illustrated in FIG. 23, the lumen tubes that surround the sub lumens 101L to 105L and the sub lumens 107L to 111L of the outer tube 10 enter the inner portion of the Y-connector 20 from the proximal end of the outer tube 10.

Figure 24:
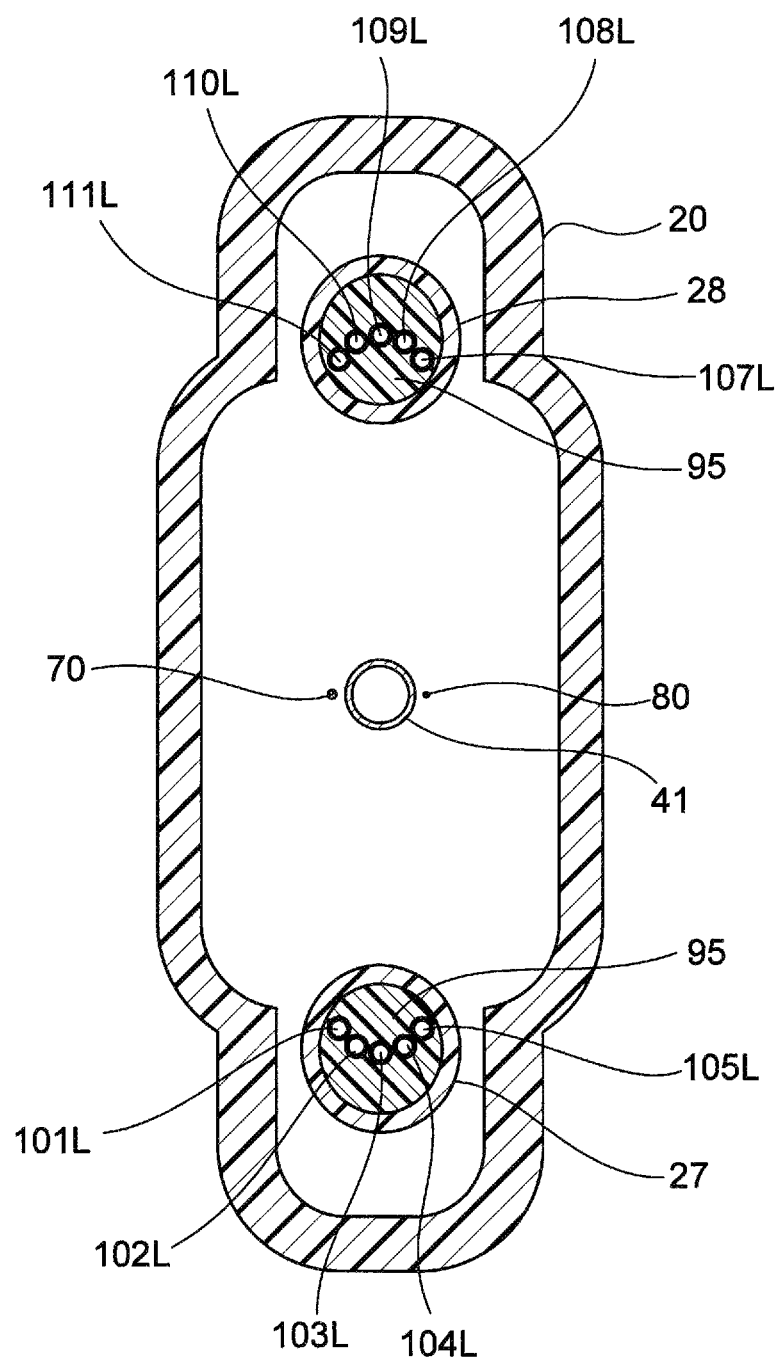
FIG. 24 is a XXIV-XXIV sectional view of FIG. 1.

As illustrated in FIG. 24, the proximal end portions of the lumen tubes that surround the sub lumens 101L to 105L (fluid supply sub lumens) are coupled (fixed by an adhesive 95) to the fluid supply tube 27 having a single lumen structure in the inner portion of the Y-connector 20.

The fluid supply tube 27 extends out to the outside of the Y-connector 20, and the proximal end of the fluid supply tube 27 is coupled to the fluid supply connector 22.

The proximal end portions of the lumen tubes that surround the sub lumens 107L to 111L are coupled (fixed by the adhesive 95) to the fluid drainage tube 28 having a single lumen structure in the inner portion of the Y-connector 20.

This fluid drainage tube 28 extends out to the outside of the Y-connector 20, and the proximal end of the fluid drainage tube 28 is coupled to the fluid drainage connector 23.

The balloon 30 that constitutes the balloon-type electrode catheter 100 is constituted by the expansion portion 31 that expands and contracts, the distal-end-side neck portion 33 continuous with the distal end of the expansion portion 31, and the proximal-end-side neck portion 35 continuous with the proximal end of the expansion portion 31.

The expansion portion 31 of the balloon 30 is a space formation part that expands as a result of a fluid being supplied into the inner portion thereof and that contracts as a result of the fluid being drained from the inner portion thereof.

As illustrated in FIG. 1 to FIG. 5, the expansion portion 31 of the balloon 30 is formed by a cylindrical part 311, a distal-end-side cone part 313 extending from the distal end of the cylindrical part 311 to the proximal end of the distal-end-side neck portion 33, and a proximal-end-side cone part 315 extending from the proximal end of the cylindrical part 311 to the distal end of the proximal-end-side neck portion 35.

As a result of the proximal-end-side neck portion 35 being fixed to the distal end portion (the distal end portion constituted by the circular tubular part 11) of the outer tube 10, and the distal end portion (the distal end portion constituted by the semicircular tubular part 13) of the outer tube 10 being contained by the expansion portion 31, the balloon 30 is connected to the distal end side of the outer tube 10.

Here, the distal end portion (the circular tubular part 11 illustrated in FIG. 19) of the outer tube 10 to which the proximal-end-side neck portion 35 of the balloon 30 is fixed has a surface layer part that is shaved, and the outer diameter of the distal end portion is smaller than the outer diameter of the proximal end portion (the circular tubular part 11 illustrated in FIG. 21) of the outer tube 10 to which the proximal-end-side neck portion 35 is not fixed.

In addition, the outer diameter of the proximal-end-side neck portion 35 illustrated in FIG. 19 is substantially equal to the outer diameter of the proximal end portion of the outer tube 10 illustrated in FIG. 21.

Consequently, it is possible to prevent insertion properties with respect to the lumens of a sheath and an endoscope that are used to introduce the balloon-type electrode catheter 100 from being impaired by the proximal-end-side neck portion 35.

In addition, the outer diameter of the outer tube 10 can be the maximum diameter restricted by the sheath and the endoscope (it is not necessary to consider the increase of the outer diameter caused by the thickness of the proximal-end-side neck portion). Thus, it is possible to sufficiently ensure the diameters of the sub lumens 101L to 112L of the outer tube 10, and it is possible to further improve the effect of cooling the inner portion of the balloon 30.

As illustrated in FIG. 3 and FIG. 4, the distal end surface 14 of the semicircular tubular part 13 in which the fluid supply sub lumens 101L to 105L open is located in the vicinity of the distal end of the cylindrical part 311, which is on the distal end side from an intermediate location in the axial direction in the expansion portion 31 of the balloon 30.

Consequently, the fluid that flows in the fluid supply sub lumens 101L to 105L is discharged in the distal end direction through each of the openings located in the vicinity of the distal end of the cylindrical part 311. The discharged fluid can reach the vicinity of the distal end of the expansion portion 31 (distal-end-side cone part 313) and, consequently, it is possible to form the flow of the fluid from the distal end side toward the proximal end side in the inner portion of the balloon 30 (expansion portion 31).

If the opening locations of the fluid supply sub lumens are present on the proximal end side from the intermediate location in the axial direction in the expansion portion of the balloon, it is not possible to cause a fluid to reach the vicinity of the distal end of the expansion portion even when the fluid is discharged in the distal end direction through the openings after the expansion of the balloon, and it is not possible to form the flow of the fluid from the distal end side toward the proximal end side in the inner portion of the balloon.

Figure 5:
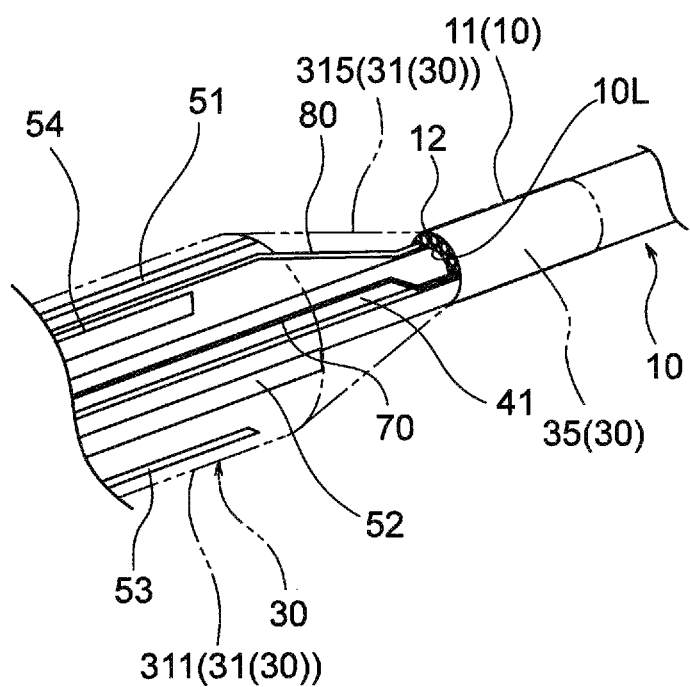
FIG. 5 is a perspective view illustrating the distal end part (the proximal end side of the balloon) of the balloon-type electrode catheter illustrated in FIG. 1.
Figure 6:
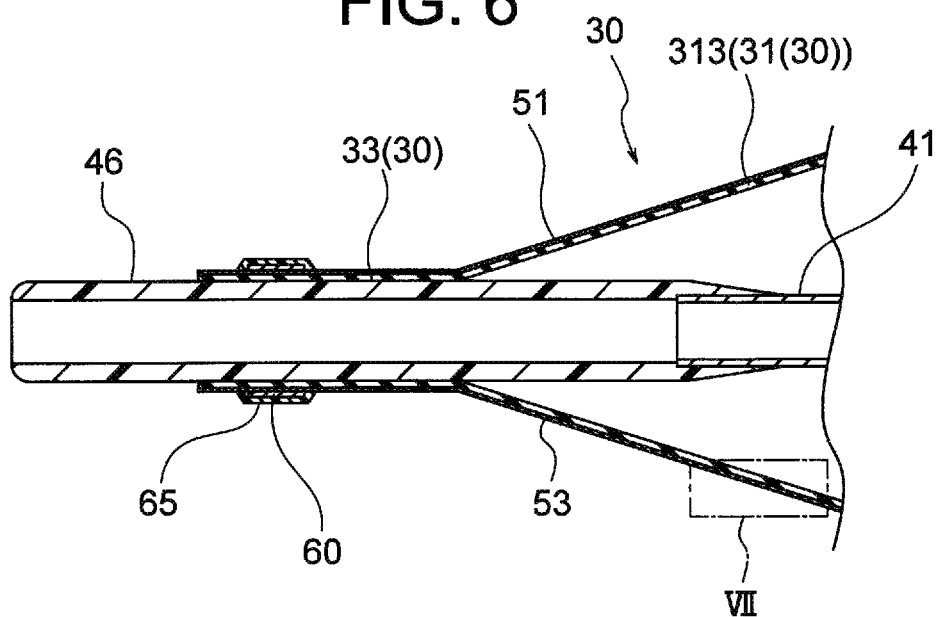
FIG. 6 is a partially enlarged view (VI portion detail illustration) of FIG. 2.
Figure 7:
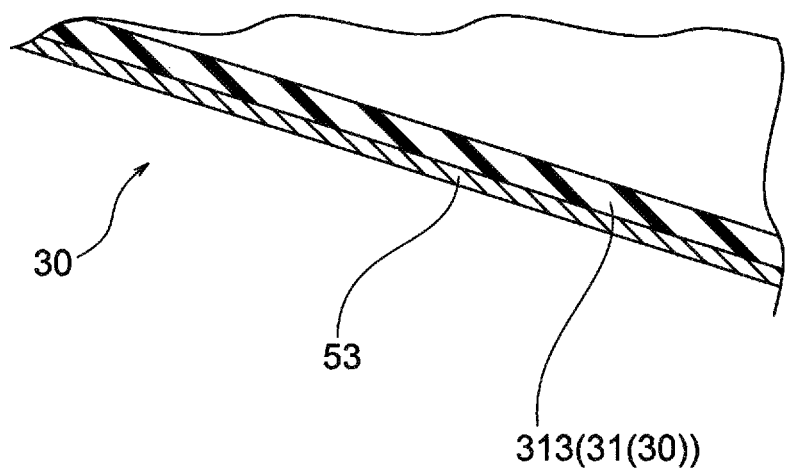
FIG. 7 is a partially enlarged view (VII portion detail illustration) of FIG. 6.
Figure 8:
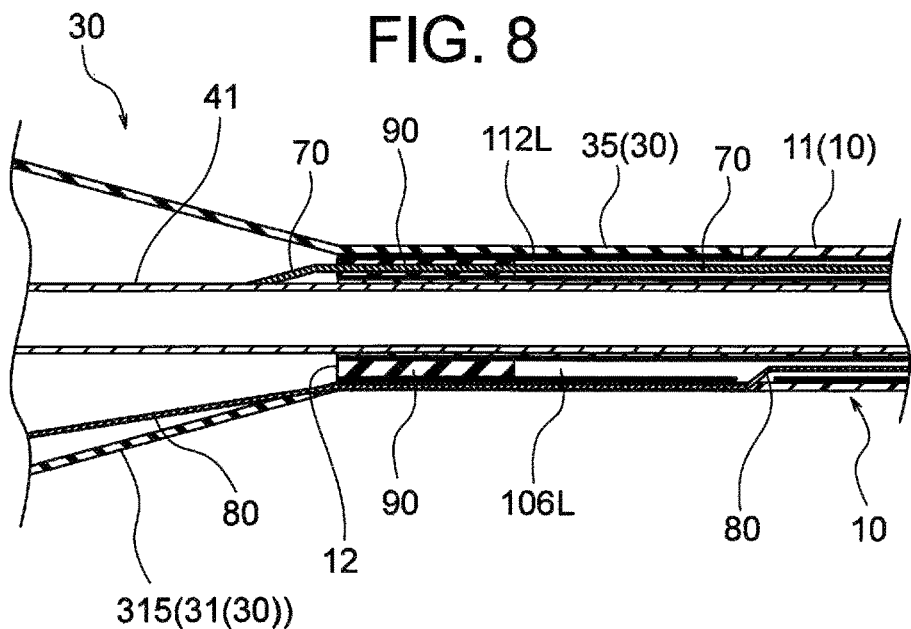
FIG. 8 is a partially enlarged view (VIII portion detail illustration) of FIG. 2.

As illustrated in FIG. 3 and FIG. 5, the distal end surface 12 of the circular tubular part 11 in which the fluid drainage sub lumens 107L to 109L and 111L open is located at the proximal end of the expansion portion 31.

The constituent material of the balloon 30 is not particularly limited, and as such a constituent material, a material identical to that of a balloon that constitutes a hitherto publicly known balloon catheter can be used. For example, polyamide resins, such as polyamide, polyether polyamide, PEBAX, nylon, and the like; and polyurethane resins, such as thermoplastic polyether urethane, polyether polyurethane urea, fluorine polyether urethane urea, polyether polyurethane urea resin, polyether polyurethane urea amide, and the like, can be presented.

The diameter of the balloon 30 (expansion portion 31) is normally 0.70 to 30.0 mm and, when one suitable example is presented, 2.0 mm.

The outer diameter of the proximal-end-side neck portion 35 of the balloon 30 is substantially equal to the outer diameter of the proximal end portion of the outer tube 10 and normally 1.0 to 3.3 mm, and, when one suitable example is presented, 1.45 mm.

The length of the balloon 30 (expansion portion 31) is normally 8 to 50 mm and, when one suitable example is presented, 20 mm.

In the balloon-type electrode catheter 100 of the present embodiment, the inner tube 41 and the distal end tip 46 constitute the inner shaft.

The inner tube 41 that constitutes the balloon-type electrode catheter 100 has a lumen (guide wire lumen) into which a guide wire is insertable. The inner tube 41 is inserted into the center lumen 10L of the outer tube 10

(circular tubular part 11), and the distal end portion thereof extends out through the opening of the center lumen 10L into the inner portion of the balloon 30 (expansion portion 31).

The distal end portion of the inner tube 41 extending out into the inner portion of the balloon 30 (expansion portion 31) extends in a state in which a half circumference part of the outer circumferential surface thereof is covered by the semicircular tubular part 13 in the inner portions of the proximal-end-side cone part 315, the cylindrical part 311, and the distal-end-side cone part 313 of the expansion portion 31. The distal end portion of the inner tube 41 is coupled to the distal end tip 46 in the inner portion of the distal-end-side cone part 313.

Meanwhile, as illustrated in FIG. 23 and FIG. 24, the proximal end portion of the inner tube 41 enters the inner portion of the Y-connector 20 from the proximal end (the opening on the proximal end side of the center lumen 10L) of the outer tube 10, extends in the inner portion of the Y-connector 20, and extends out to the outside of the Y-connector 20. The proximal end of the inner tube 41 is coupled to the guide wire connector 24.

As the constituent material of the inner tube 41, a material identical to that of an inner tube that constitutes a hitherto publicly known balloon catheter can be used. A PEEK resin (polyether ether ketone resin), which is a crystalline thermoplastic resin excellent in mechanical properties, is preferable.

The outer diameter of the inner tube 41 is identical to or slightly smaller than the diameter of the center lumen 10L of the outer tube 10 into which the inner tube 41 is inserted and is normally 0.34 to 0.99 mm and, when one suitable example is presented, 0.84 mm.

The inner diameter of the inner tube 41 is normally 0.31 to 0.92 mm and, when one suitable example is presented, 0.68 mm.

The distal end tip 46 that constitutes the balloon-type electrode catheter 100 has a lumen (guide wire lumen) in communication with the guide wire lumen of the inner tube 41, is connected to the distal end of the inner tube 41 in the inner portion of the distal-end-side cone part 313 of the expansion portion 31 of the balloon 30, fixed to the distal-end-side neck portion 33, and extends to the outside of the balloon 30.

The constituent material of the distal end tip 46 is not particularly limited, and as such a constituent material, for example, polyamide resins, such as polyamide, polyether polyamide, PEBAX, nylon, and the like, polyurethane, and the like can be presented.

The inner diameter of the distal end tip 46 is substantially identical to the inner diameter of the inner tube 41 and is normally 0.31 to 0.92 mm and, when one suitable example is presented, 0.68 mm.

The outer diameter of the distal end tip 46 is normally 0.35 to 2.6 mm and, when one suitable example is presented, 1.0 mm.

The outer diameter of the distal-end-side neck portion 33 of the balloon 30 to which the distal end tip 46 is fixed is normally 0.37 to 3.3 mm and, when one suitable example is presented, 1.18 mm.

As illustrated in FIG. 3 to FIG. 7 and FIG. 9 to FIG. 15, on the outer surface of the balloon 30 (the cylindrical part 311 and the distal-end-side cone part 313 of the expansion portion 31, and the distal-end-side neck portion 33), the strip electrodes 51 to 54 that are formed by a metal thin film so as to extend in the axial direction of the balloon 30 are disposed, as surface electrodes that are to be energized with high-frequency current, in the circumferential direction of the balloon 30 at 90° intervals.

As the constituent material of the metal thin film that constitutes the strip electrodes 51 to 54, gold, platinum, silver, copper, alloys thereof, stainless steel, and the like can be presented.

The film thickness of the metal thin film that constitutes the strip electrodes 51 to 54 is preferably 0.5 to 5 μm and more preferably 1.0 to 2.5 μm.

When the film thickness is excessively small, there is a possibility of the metal thin film being caused to have a high temperature by Joule heat during manipulation (during high-frequency energization).

Moreover, when the film thickness of the thin film is excessively large, the metal thin film does not easily follow a change in the shape of the balloon along with expansion and contraction, and there is a likelihood of the expansion-contraction properties of the balloon being impaired.

A method of forming the metal thin film that constitutes the strip electrodes 51 to 54 on the outer surface of the balloon 30 is not particularly limited, and as such a method, a normal metal-thin-film formation method, such as vapor deposition, sputtering, plating, printing, and the like, can be employed.

As illustrated in FIG. 3, FIG. 4, FIG. 6, FIG. 9, and FIG. 10, the metal ring 60 is mounted on the distal-end-side neck portion 33 of the balloon 30.

The metal ring 60 that constitutes the balloon-type electrode catheter 100 is fixed by crimping to the distal-end-side neck portion 33 such that the inner circumferential surface thereof is in contact with the distal end portion of each of the strip electrodes 51 to 54. Consequently, each of the strip electrodes 51 to 54 and the metal ring 60 are electrically connected to each other.

Figure 9:
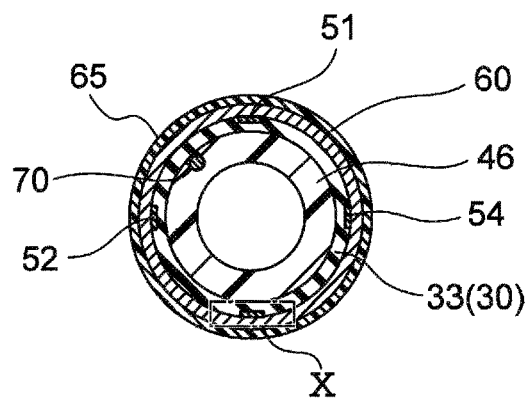
FIG. 9 is a IX-IX sectional view of FIG. 1.
Figure 10:
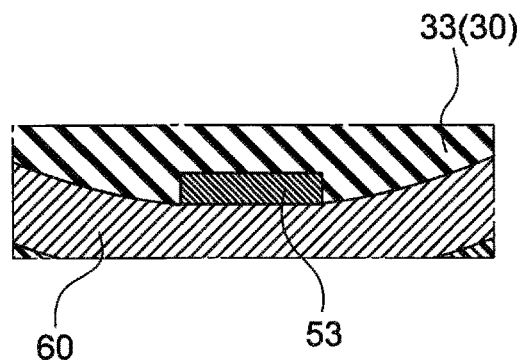
FIG. 10 is a partially enlarged view (X portion detail illustration) of FIG. 9.

As the constituent material of the metal ring 60, platinum, platinum-based alloys, and the like can be presented. As illustrated in FIG. 9, the metal ring 60 is insulation coated by a resin material 65. Consequently, it is possible to prevent the metal ring 60 during energization from having a high temperature, and it is possible to prevent the normal tissue around the metal ring 60 from being ablated.

The inner diameter of the metal ring 60 mounted on the distal-end-side neck portion 33 is substantially identical to the outer diameter of the distal-end-side neck portion 33. The inner diameter of the metal ring 60 is normally 0.37 to 3.3 mm and, when one suitable example is presented, 1.18 mm.

The outer diameter of the metal ring 60 mounted on the distal-end-side neck portion 33 is smaller than the outer diameter of the outer tube 10 or the proximal-end-side neck portion 35. The outer diameter of the metal ring 60 is normally 0.98 to 3.28 mm and, when one suitable example is presented, 1.32 mm.

The distal end of the conducting wire 70 is fixed to the inner circumferential surface of the metal ring 60.

Figure 11:
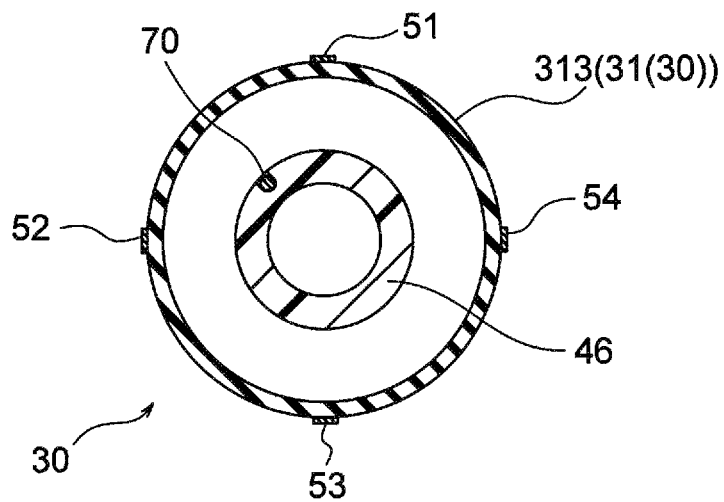
FIG. 11 is a XI-XI sectional view of FIG. 1.
Figure 12:
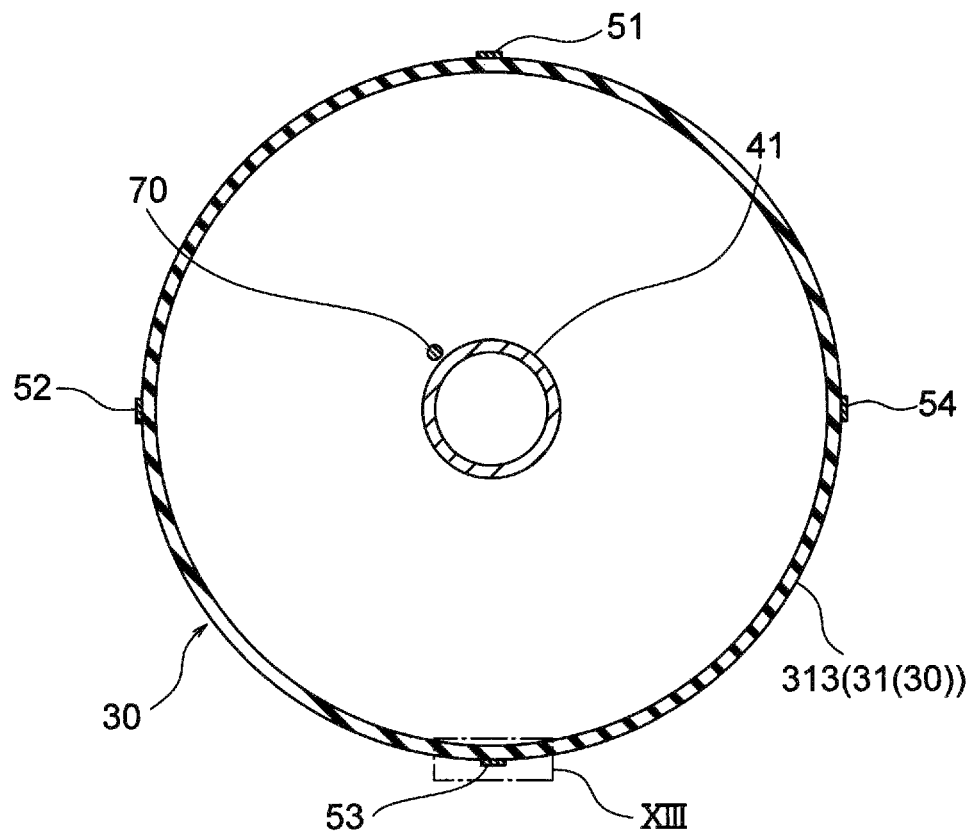
FIG. 12 is a XII-XII sectional view of FIG. 1.
Figure 13:
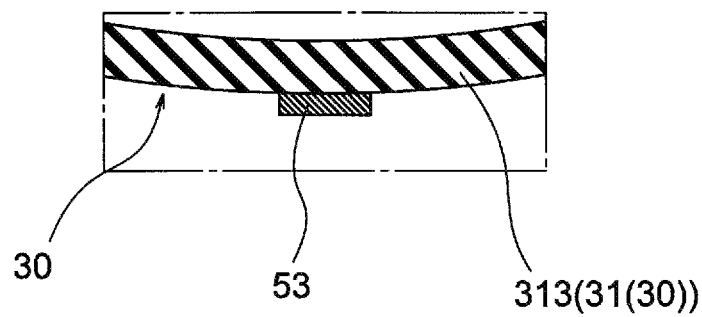
FIG. 13 is a partially enlarged view (XIII portion detail illustration) of FIG. 12.

The conducting wire 70 extends as illustrated in FIG. 9 and FIG. 11 in the tube wall of the distal end tip 46, extends as illustrated in FIG. 12, FIG. 14, and FIG. 15 along the inner tube 41 in the inner portion of the expansion portion 31 of the balloon 30, extends as illustrated in FIG. 17, FIG. 19, and FIG. 21 in the sub lumen 112L of the outer tube 10 (circular tubular part 11), extends as illustrated in FIG. 23 and FIG. 24 in the inner portion of the Y-connector 20, and extends out from the Y-connector 20 through the inner portion of a conducting-wire protection tube 26 that extends out from the Y-connector 20.

The proximal end of the conducting wire 70 is connected to the electrical connector 21. The electrical connector 21 has both a function as an energization connector that energizes each of the strip electrodes 51 to 54 with high-frequency current and a function as a thermocouple connector for connecting the temperature sensor 80 to a temperature measuring instrument.

By connecting each of the strip electrodes 51 to 54 to the electrical connector 21 via the metal ring 60 and the conducting wire 70, it is possible to equally energize each of the strip electrodes 51 to 54 with the high-frequency current.

As the constituent material of the conducting wire 70, for example, copper, silver, gold, platinum, tungsten, and alloys of these metals can be presented, and, preferably, electrical insulation protection coating of fluororesin or the like is applied thereto.

As illustrated in FIG. 3, FIG. 5, and FIG. 15 to FIG. 20, the temperature sensor 80 formed by the thermocouple is disposed to be embedded in the tube wall of the balloon 30. The temperature measuring portion 81 (temperature measurement contact point) of the temperature sensor 80 is located at the tube wall of the expansion portion 31.

As illustrated in FIG. 19 to FIG. 22, the temperature sensor 80 enters the sub lumen 106L of the outer tube 10 (circular tubular part 11) from the tube wall of the proximal-end-side neck portion 35 of the balloon 30 and extends in the sub lumen 106L. Then, as illustrated in FIG. 23 and FIG. 24, the temperature sensor 80 extends together with the conducting wire 70 in the inner portion of the Y-connector 20 and extends out from the Y-connector 20 through the inner portion of the conducting-wire protection tube 26 that extends out from the Y-connector 20.

The proximal end of the temperature sensor 80 is connected to the electrical connector 21.

According to the balloon-type electrode catheter 100 of the present embodiment, it is possible by each of the strip electrodes 51 to 54 formed on the outer surface of the balloon 30 to perform a high frequency ablation treatment over a wide area with respect to a lesion in a vessel or around the vessel.

In addition, as a result of each of the fluid supply sub lumens 101L to 105L opening in the distal end surface 14 of the semicircular tubular part 13 located in the vicinity of the distal end of the cylindrical part 311 of the expansion portion 31 of the balloon 30, and each of the fluid drainage sub lumens 107L to 109L and 111L opening in the distal end surface 12 of the circular tubular part 11 located at the proximal end of the expansion portion 31 of the balloon 30, it is possible, even after expansion of the balloon 30 (after the inner portion is filled with a fluid), to form the flow of a fluid from the distal end side toward the proximal end side in the inner portion of the balloon 30 and to cause the fluid to flow.

In particular, as a result of the fluid that is discharged in the distal end direction through the openings of the fluid supply sub lumens 101L to 105L coming into contact with the inner wall surface of the distal-end-side cone part 313 of the expansion portion 31 and then flowing in the proximal end direction along the inner wall surfaces of the cylindrical part 311 and the proximal-end-side cone part 315 of the expansion portion 31, it is possible to circulate the fluid in the inner portion of the balloon 30 (expansion portion 31).

As a result, it is possible to efficiently cool the inner portion of the balloon 30 over the whole region of the expansion portion 31. Consequently, the tissue around the strip electrodes 51 to 54 is sufficiently cooled, and it is possible to reliably prevent the tissue from being fiberized.

In addition, the number of the fluid supply sub lumens 101L to 105L disposed in the outer tube 10 is five, and the number of the fluid drainage sub lumens 107L to 109L and 111L is four. Thus, it is possible to maintain the inner portion of the balloon 30 at a constant pressure (expansion pressure).

In addition, as a result of the metal ring 60 being mounted on the distal-end-side neck portion of the balloon 30 such that the inner circumferential surface thereof is in contact with the distal end portion of each of the strip electrodes 51 to 54, each of the strip electrodes 51 to 54 is electrically connected to the electrical connector 21 via the metal ring 60 and the conducting wire 70. Therefore, it is possible to energize each of the strip electrodes 51 to 54 equally with high-frequency current. Consequently, it is possible to homogeneously perform an ablation treatment of a lesional tissue in a vessel or around the vessel in the circumferential direction of the vessel.

In addition, because the outer diameter of the metal ring 60 mounted on the distal-end-side neck portion 33 of the balloon 30 is smaller than the outer diameters of the proximal-end-side neck portion 35 and the outer tube 10, the metal ring 60 is not caught by openings of a sheath and an endoscope that are used during introduction, and the insertion properties of the balloon-type electrode catheter 100 with respect to the lumens of the sheath and the endoscope are not impaired.

Cases to which the balloon-type electrode catheter 100 of the present embodiment is applicable are, for example, tumors, vagus nerve, and the like in a vessel or around the vessel. Specifically, as such cases, bile duct cancer, lung cancer, liver cancer, kidney cancer, adrenal adenoma, renal artery vagus nerve, and the like can be presented.

Second Embodiment

A balloon-type electrode catheter 200 of this embodiment is a balloon-type electrode catheter that is to be percutaneously introduced to treat a lesional tissue, such as a tumor and the like, by high frequency ablation.

In FIG. 25, which illustrates the distal end part of the balloon-type electrode catheter 200, the parts indicated by signs identical to those in FIG. 3 to FIG. 5 and parts that are not illustrated have the same configurations as those in the first embodiment, and description thereof is omitted.

The balloon-type electrode catheter 200 of the present embodiment is provided with the outer tube 10 that is formed by the circular tubular part 11 and the semicircular tubular part 13 and that has the center lumen 10L and sub lumens (101L to 112L) disposed around the center lumen 10L; the electrical connector (21) disposed on the proximal end side of the outer tube 10; the balloon 30 that has the expansion portion 31 that expands and contracts, and neck portions (the distal-end-side neck portion 33 and the proximal-end-side neck portion 35) continuous with both ends thereof, the balloon 30 being connected to the distal end side of the outer tube 10 as a result of the proximal-end-side neck portion 35 being fixed to the circular tubular part 11 that constitutes the distal end portion of the outer tube 10 and the expansion portion 31 containing the semicircular tubular part 13 that constitutes the distal end portion of the outer tube 10; an inner shaft 47 that is formed by a solid metal needle that is inserted into the center lumen 10L of the outer tube 10, extends out through an opening of the center lumen 10L into the inner portion of the balloon 30 (expansion portion 31), is fixed to the distal-end-side neck portion 33 of the balloon 30, and extends out to the outside of the balloon 30, the metal needle having a needle tip portion 48 at the distal end thereof and being electrically connected at the rear end thereof to the electrical connector 21; the strip electrodes 51 to 54 (surface electrodes) formed by a metal thin film formed on the outer surfaces of the expansion portion 31 and the distal-end-side neck portion 33 of the balloon 30; a metal ring 67 that is mounted so as to straddle between the distal-end-side neck portion 33 of the balloon 30 and the distal end portion of the inner shaft 47 extending out from the balloon 30, so that each of the strip electrodes 51 to 54 is electrically connected to the electrical connector 21 via the inner shaft 47; and the temperature sensor (thermocouple) 80.

The balloon-type electrode catheter 200 of the present embodiment differs from the balloon-type electrode catheter 100 of the first embodiment in terms of the inner shaft 47 that constitutes the balloon-type electrode catheter 200 being formed by the solid metal needle.

The inner shaft 47 formed by the metal needle has a function of a conducting wire that electrically connects each of the strip electrodes 51 to 54 and the electrical connector 21 to each other.

According to the balloon-type electrode catheter 200 of the present embodiment, it is possible to exert the same effects as those of the balloon-type electrode catheter 100 of the first embodiment.

That is, it is possible to perform a high frequency ablation treatment over a wide area by each of the strip electrodes 51 to 54 formed on the outer surface of the balloon 30.

In addition, it is possible to efficiently cool the inner portion of the balloon 30 over the whole region of the expansion portion 31. Consequently, the tissue around the strip electrodes 51 to 54 is sufficiently cooled, and it is possible to reliably prevent the tissue from being fiberized.

Further, it is possible to maintain the inner portion of the balloon 30 at a constant pressure (expansion pressure).

The balloon-type electrode catheter 200 of the present embodiment can be percutaneously introduced, in a state in which the contracted balloon 30 is wrapped, into a lesion by utilizing the inner shaft 47 formed by the metal needle and can perform an ablation treatment over a wide area with respect to the lesion by expanding the balloon 30 after introduction and energizing the strip electrodes 51 to 54.

As cases to which the balloon-type electrode catheter 100 of the present embodiment is applicable, lung cancer, liver cancer, kidney cancer, adrenal adenoma, and the like can be presented.

Although embodiments of the present invention have been described above, the present invention is not limited to these embodiments and can be variously changed.

For example, the location (the opening locations of the fluid supply sub lumens 101L to 105L) of the distal end surface 14 of the semicircular tubular part 13 in the inner portion of the balloon 30 is not limited to being in the vicinity of the distal end of the cylindrical part 311 of the expansion portion 31 as long as being on the distal end side from the intermediate location in the axial direction in the expansion portion 31.

In addition, in the balloon-type electrode catheter according to the present invention, the openings of the fluid supply sub lumens and/or the fluid drainage sub lumens may be formed in the outer circumferential surface of the outer tube, and a fluid may be discharged/drained in the radial direction of the outer tube.

In addition, the openings of the fluid supply sub lumens may be located at the proximal end of the expansion portion of the balloon or in the vicinity thereof, and the openings of the fluid drainage sub lumens may be located on the distal end side from the intermediate location in the axial direction in the expansion portion.

REFERENCE SIGNS LIST

100 balloon-type electrode catheter
10 outer tube
10L center lumen
101L to 105L sub lumen (fluid supply sub lumen)
107L to 109L, 111L sub lumen (fluid drainage sub lumen)
106L, 110L, 112L sub lumen
11 circular tubular part
12 distal end surface of circular tubular part
13 semicircular tubular part
14 distal end surface of semicircular tubular part
20 Y-connector
21 electrical connector
22 fluid supply connector
23 fluid drainage connector
24 guide wire connector
26 conducting-wire protection tube
27 fluid supply tube
28 fluid drainage tube
30 balloon
31 expansion portion
311 cylindrical part 311
313 distal-end-side cone part 313
315 proximal-end-side cone part 315
33 distal-end-side neck portion
35 proximal-end-side neck portion
41 inner tube
46 distal end tip
51 to 54 strip electrode (surface electrode)
60 metal ring
70 conducting wire
80 temperature sensor (thermocouple)
81 temperature measuring portion of temperature sensor
90 seal material
200 balloon-type electrode catheter
47 inner shaft
48 needle tip portion
67 metal ring

The invention claimed is:

1. A balloon-type electrode catheter for performing a high frequency ablation treatment, the balloon-type electrode catheter comprising :
    an outer tube that has a center lumen and a plurality of sub lumens that are disposed around the center lumen;
    an energization connector that is disposed on a proximal end side of the outer tube;
    a balloon that has an expansion portion that expands and contracts and a proximal-end-side neck portion and a distal-end-side neck portion, wherein the proximal-end-side neck portion is continuous with an end of the expansion portion and the distal-end-side neck portion is continuous with another end of the expansion portion, the balloon being connected to a distal end side of the outer tube as a result of the proximal-end-side neck portion being fixed to a distal end portion of the outer tube and the expansion portion containing the distal end portion of the outer tube;
    an inner shaft that is inserted into the center lumen of the outer tube, the inner shaft extending out through an opening of the center lumen into an inner portion of the balloon, being fixed to the distal-end-side neck portion of the balloon, and extending out to an outside of the balloon;

a surface electrode that is formed by a metal thin film that is formed on an outer surface of the balloon at at least the expansion portion of the balloon; and a conducting wire that electrically connects the surface electrode and the energization connector to each other, wherein at least one of the sub lumens of the outer tube is a fluid supply sub lumen in which a fluid, including physiological saline solution, is caused to flow to supply the fluid into the inner portion of the balloon, wherein at least one of the sub lumens of the outer tube is a fluid drainage sub lumen in which the fluid is caused to flow to drain the fluid supplied into the inner portion of the balloon, from the inner portion of the balloon, wherein an opening of either one of the fluid supply sub lumen and the fluid drainage sub lumen is located on a distal end side further from an intermediate location in an axial direction in the expansion portion, wherein an opening of the other of the fluid supply sub lumen and the fluid drainage sub lumen is located at a proximal end of the expansion portion or in a vicinity thereof, wherein the opening of the fluid supply sub lumen is located on the distal end side from the intermediate location in the axial direction in the expansion portion, wherein the opening of the fluid drainage sub lumen is located at the proximal end of the expansion portion or in a vicinity thereof, wherein the outer tube is formed by
a circular tubular part that extends in a proximal end direction from the proximal end of the expansion portion or a location in a vicinity thereof, and
a semicircular tubular part that extends in a distal end direction from the proximal end of the expansion portion or a location in the vicinity thereof in an inner portion of the expansion portion beyond the intermediate location in the axial direction in the expansion portion, wherein the fluid supply sub lumen is disposed in inner portions of the circular tubular part and the semicircular tubular part and opens in a distal end surface of the semicircular tubular part, and wherein the fluid drainage sub lumen is disposed in the inner portion of the circular tubular part and opens in a distal end surface of the circular tubular part.

2. The balloon-type electrode catheter according to claim 1,
wherein an opening area of the fluid supply sub lumen is larger than an opening area of the fluid drainage sub lumen.

3. The balloon-type electrode catheter according to claim 1,
wherein a number of the fluid supply sub lumen is greater than a number of the fluid drainage sub lumen.

4. The balloon-type electrode catheter according to claim 1,
wherein the inner shaft is formed by an inner tube that has a lumen into which a guide wire is insertable and that is inserted into the center lumen of the outer tube and extends out through the opening of the center lumen into the inner portion of the balloon, and a distal end tip that has a lumen in communication with the lumen of the inner tube and that is, while being connected to a distal end of the inner tube in the inner portion of the balloon, fixed to the distal-end-side neck portion and extends out to the outside of the balloon.

5. The balloon-type electrode catheter according to claim 4,
wherein a distal end portion of the surface electrode extends on an outer surface of the distal-end-side neck portion, wherein a metal ring is provided, the metal ring being electrically connected to the surface electrode by being mounted on the distal-end-side neck portion of the balloon such that an inner circumferential surface of the metal ring is in contact with the distal end portion of the surface electrode, and wherein a distal end of the conducting wire is connected to the inner circumferential surface of the metal ring, the conducting wire extends in the inner portion of the balloon and in the sub lumens of the outer tube, the sub lumens being different from either of the fluid supply sub lumen and the fluid drainage sub lumen, and a proximal end of the conducting wire is connected to the energization connector.

6. The balloon-type electrode catheter according to claim 5,
wherein the surface electrode is a plurality of strip electrodes that are formed so as to extend in an axial direction of the balloon and that are disposed in a circumferential direction of the balloon at equal angular the inner intervals, and circumferential surface of the metal ring is in contact with a distal end portion of each of the strip electrodes.

7. The balloon-type electrode catheter according to claim 5,
wherein the metal ring is insulation coated.

8. The balloon-type electrode catheter according to claim 1,
wherein the inner shaft is formed by a hollow or solid needle.

9. The balloon-type electrode catheter according to claim 1,
wherein an outer diameter of the distal end portion of the outer tube to which the proximal-end-side neck portion of the balloon is fixed is formed to be smaller than an outer diameter of a proximal end portion of the outer tube, and wherein an outer diameter of the proximal-end-side neck portion of the balloon and the outer diameter of the proximal end portion of the outer tube are substantially equal to each other.

10. The electrode catheter according to claim 1,
wherein a temperature sensor is disposed at a tube wall of the balloon.

* * * * *